(12) United States Patent
Yamazaki et al.

(10) Patent No.: US 6,944,266 B2
(45) Date of Patent: Sep. 13, 2005

(54) X-RAY IMAGING APPARATUS

(75) Inventors: Tatsuya Yamazaki, Tochigi (JP); Masakazu Morishita, Kanagawa (JP); Isao Kobayashi, Kanagawa (JP); Osamu Tsujii, Tochigi (JP); Akira Hirai, Tochigi (JP); Toshikazu Tamura, Tochigi (JP); Hideki Nonaka, Tochigi (JP); Takamasa Ishii, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/685,534

(22) Filed: Oct. 16, 2003

(65) Prior Publication Data

US 2004/0096035 A1 May 20, 2004

(30) Foreign Application Priority Data

Nov. 15, 2002 (JP) ...................................... 2002-332576

(51) Int. Cl.[7] .............................................. H05G 1/64
(52) U.S. Cl. ...................... 378/98.7; 378/98.8; 378/155
(58) Field of Search ............................... 378/98.7, 98.8, 378/108, 154, 155, 62, 901, 116, 151, 16; 250/370.09, 370.08

(56) References Cited

U.S. PATENT DOCUMENTS

| | | | |
|---|---|---|---|
| 5,379,335 A | * | 1/1995 | Griesmer et al. ............ 378/155 |
| 5,825,032 A | | 10/1998 | Nonaka et al. ......... 250/370.09 |
| 6,047,042 A | * | 4/2000 | Khutoryansky et al. ....... 378/62 |
| 6,404,851 B1 | * | 6/2002 | Possin et al. ............... 378/98.7 |
| 6,459,765 B1 | * | 10/2002 | Ganin et al. ................. 378/108 |
| 6,553,095 B2 | * | 4/2003 | Rinaldi et al. ............... 378/108 |
| 6,850,597 B2 | | 2/2005 | Matsumoto et al. ......... 378/154 |
| 2002/0012450 A1 | | 1/2002 | Tsujii | |

* cited by examiner

Primary Examiner—Edward J. Glick
Assistant Examiner—Irakli Kiknadze
(74) Attorney, Agent, or Firm—Fitzpatrick, Cella, Harper & Scinto (57) ABSTRACT

An X-ray imaging apparatus including an X-ray generation means for emitting X-rays, and an X-ray detector on which a grid selected from a plurality of different types of grids is removably mountable. The X-ray detector receives the X-rays emitted from the X-ray generation means, and obtains an X-ray image. The X-ray detector includes an automatic exposure control (AEC) detector for detecting the quantity of X-rays emitted from the X-ray generation means and for outputting a signal based on the detected quantity. The X-ray imaging apparatus also includes a control means for controlling the X-ray generation means and the AEC detector, where the control means controls the X-ray generation means based on the signal output from the AEC detector, and where the control means controls the AEC detector using correction data to correct an exposure detection element forming a part of the AEC detector.

12 Claims, 4 Drawing Sheets

X-RAY IMAGING APPARATUS

BACKGROUND OF THE INVENTION

1. Field of the Invention

The present invention relates to an X-ray imaging apparatus having at least one automatic exposure control (AEC) pixel for performing real-time detection for part of an X ray that is made incident via a subject. The X-ray imaging apparatus performs AEC based on a signal detected by the AEC pixel, and takes an X-ray image of the subject, based on the X-ray.

2. Description of the Related Art

Figure 4:
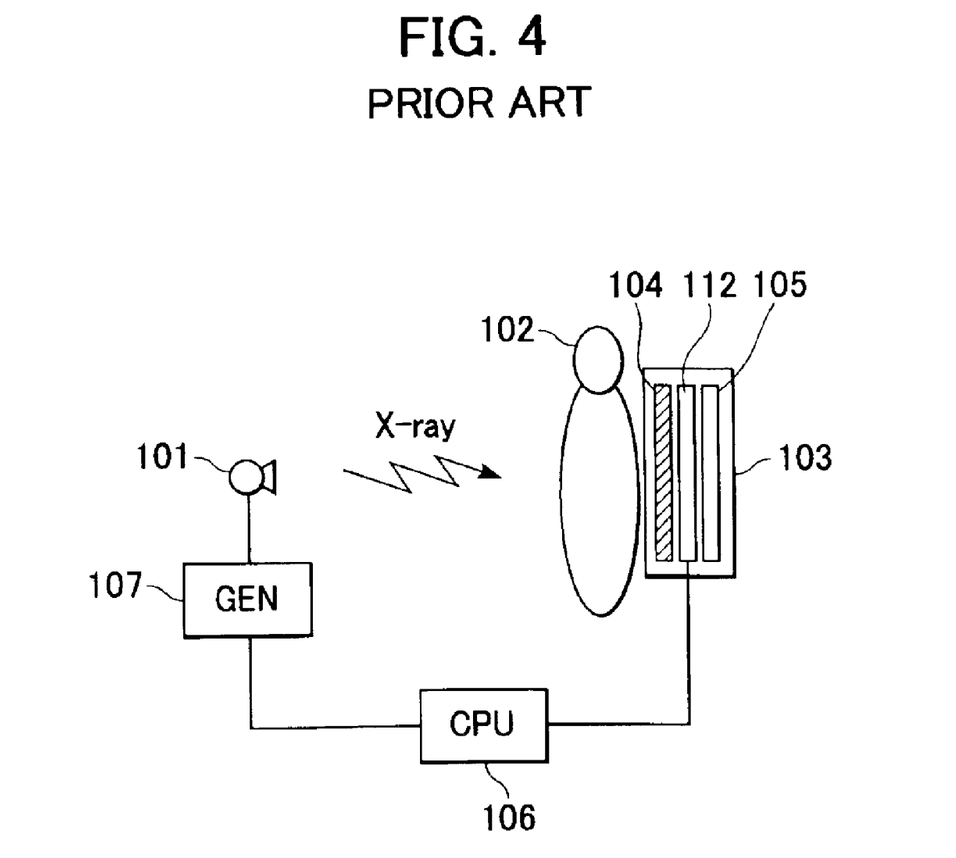
FIG. 4 is a block diagram illustrating the schematic configuration of a known X-ray imaging apparatus having AEC capability.

A known X-ray imaging apparatus will be described with reference to FIG. 4, which depicts an X-ray tube 101, a patient 102, an imaging unit 103, a grid 104, an AEC detector 112, an X-ray detector 105, a CPU 106, and an X-ray generator 107.

When an X-ray-generation signal transmitted from the CPU 106 is turned on, the X-ray generator 107 makes the X-ray tube 101 operate so that the X-ray tube 101 generates an X-ray. The X-ray emitted from the X-ray tube 101 passes through the patient 102 as a subject and reaches the imaging unit 103. At that time, the X-ray is scattered and absorbed in the body of the patient 102. Since only primary radiation traveling straight into the body of the patient 102 can be used for imaging, scattered radiation is unnecessary for the X-ray detector 105.

Generally, the grid 104 is used for removing the unnecessary scattered radiation to improve the contrast of the X-ray image. The AEC detector 112 is used for decreasing the quantity of X-ray exposure received by a human body as much as possible and for adjusting the X-ray imaging apparatus such that a predetermined amount of X-rays are emitted. An AEC system including the above-described AEC detector 112 is often referred to as a "phototimer".

The degree of scattering and absorption of the X-ray in the patient 2 changes according to the composition of the body of the patient 102. Where the body of the patient 102 is thick, the degree of scattering and absorption is high. On the other hand, if the body of the patient 102 is thin, the degree of scattering and absorption is low. However, in comparing two patients with the same body thickness but different amounts of muscle or fat, the degree of scattering and absorption of the patients will differ.

Further, the degree of the absorption also changes according to the body part exposed to the X-ray. For example, in the case where a hand or a leg, which is thin, is exposed to the X-ray, only a small amount of scattered radiation is generated. In this case, the grid 4 is preferably removed to decrease the exposure dose.

The amount of X-rays that are made incident to the AEC detector 112 changes according to the grid state, such as whether or not the grid is mounted, the grid type, and exposure conditions affecting a grid image. Therefore, it has been difficult to correctly estimate the amount of primary radiation passing through the patient 2 before exposure, based on the amount of the X-rays that are made incident to the AEC detector 12.

SUMMARY OF THE INVENTION

Accordingly, it is an object of the present invention to provide an X-ray imaging apparatus that can correctly estimate the amount of X-rays that are made incident on the patient regardless of the state of a grid by calibrating a signal detected by an AEC pixel according to the grid state. Further, the foregoing object is also attained when the correction data is gain-correction data obtained in the case where an X-ray with known intensity distribution is emitted and/or dark-current correction data obtained in the case where no X-ray is emitted.

According to the present invention, the foregoing object is attained by providing an X-ray imaging apparatus comprising an X-ray generation unit for emitting an X-ray, an X-ray detector on which a plurality types of grids can be mounted in removable manner, the X-ray detector being used for receiving the X-ray emitted from the X-ray generation unit and for obtaining an X-ray image, an AEC detector for detecting the amount of the X-ray emitted from the X-ray generation unit, the AEC detector being included in the X-ray detector, and a control unit for controlling the X-ray generation unit based on a value relating to a signal output from the AEC detector, and the AEC detector. The control unit corrects an element forming the AEC detector by using correction data.

Thus according to one aspect of the present invention, the foregoing object is attained by providing an X-ray imaging apparatus including an X-ray generation means for emitting X-rays and an X-ray detector on which a grid selected from a plurality of different types of grids is removably mountable. The X-ray detector receives the X-rays emitted from the X-ray generation means, and obtains an X-ray image. The X-ray detector includes an automatic exposure control (AEC) detector for detecting the quantity of X-rays emitted from the X-ray generation means and for outputting a signal based on the detected quantity. The X-ray imaging apparatus also includes control means for controlling the X-ray generation means and the AEC detector, where the control means controls the X-ray generation means based on the signal output from the AEC detector, and where the control means controls the AEC detector using correction data to correct an exposure detection element forming a part of the AEC detector.

In a first preferred aspect, the correction data relates to which of the plurality of types of grids is mounted on the X-ray detector.

In a second preferred aspect, the correction data relates to a state in which none of the plurality of different types of grids is mounted.

In a third preferred aspect, the X-ray imaging apparatus also includes a storing means. In the third aspect, the control means stores the correction data in the storing means and the control means selects the correction data according to whether one of the plurality of different types of grids is mounted, and which type of the plurality of types of grids is mounted, and at least one other condition affecting the grid.

In a fourth preferred aspect, the control means further includes correction data calculation means. In the fourth aspect, the control means calculates the correction data based on the correction data stored in the storing means, in the case where no correction data corresponding to the at least one other condition is stored in the storing means.

In a fifth preferred aspect, the correction data is gain-correction data and/or dark-current correction data, where the gain correction data is obtained using X-rays with known intensity distribution and where the dark-current correction data is obtained in the case where no X-rays are emitted.

In a sixth preferred aspect, the AEC detector further includes a plurality of exposure detection elements and all of the exposure detection elements are integrated into the X-ray detector.

In a seventh preferred aspect, the AEC detector further includes a plurality of pixels, where each pixel is formed as a detector element that can be read in non-destructive manner.

In an eighth preferred aspect, the AEC detector further includes a plurality of pixels, where each pixel is formed as a thin film transistor (TFT)-detector element.

In a ninth preferred aspect, the control means reads the signal output from the AEC detector in a cycle of 5 msec or less.

In a tenth preferred aspect, the AEC detector further includes a plurality of pixels formed as stripes of detector elements provided so as to be substantially parallel to the orientation of stripes of the grid.

According to a particularly preferred aspect, a method for controlling an X-ray imaging apparatus that has at least one automatic exposure control (AEC) pixel, including the steps of detecting in real-time part of an X-ray that is made incident via a subject, performing AEC based on a signal detected by the AEC pixel, and generating an X-ray image of the subject based on the X-ray that is made incident via the subject, is provided. The method includes the steps of calibrating the signal detected by the AEC pixel according to a grid state; and performing AEC detection based on the calibrated detected signal.

According to additional preferred aspects, the invention also provides for computer-executable process steps stored on a computer-readable medium, and computer-readable medium which stores computer-executable process steps, for controlling an X-ray imaging apparatus that has at least one AEC pixel, including the steps of detecting in real-time part of an X-ray that is made incident via a subject, performing AEC based on a signal detected by the AEC pixel, and generating an X-ray image of the subject based on the X-ray that is made incident via the subject.

Further objects, features and advantages of the present invention will be apparent from the following descriptions of the preferred embodiments taken in conjunction with the accompanying drawings, in which like reference characters designate the same or similar parts throughout the figures.

BRIEF DESCRIPTION OF THE DRAWINGS

The accompanying drawings, which are incorporated in and constitute a part of the specification, illustrate embodiments of the invention and, together with the descriptions, serve to explain the principle of the invention.

DESCRIPTION OF THE PREFERRED EMBODIMENTS

Preferred embodiments of the present invention will be described in detail in accordance with the accompanying drawings.

Figure 1:
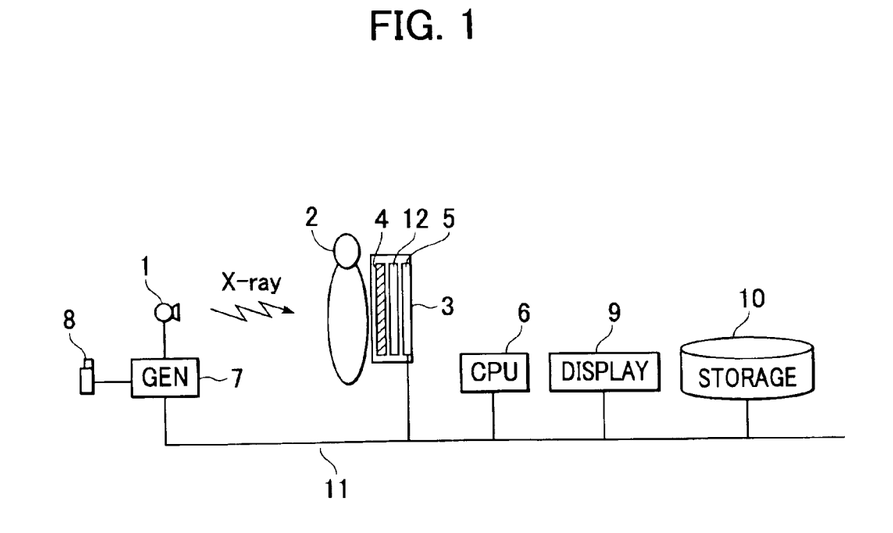
FIG. 1 is a block diagram illustrating the schematic configuration of an X-ray imaging apparatus according to an embodiment of the present invention.

FIG. 1 depicts an X-ray tube 1 for emitting an X-ray, a patient 2 as a subject, an imaging unit 3, a grid 4, an X-ray detector 5, an AEC detector 12 which is preferably formed as part of the detector 5 and which includes at least one exposure detection element such as an AEC pixel, a central processing unit (CPU) 6 for controlling the operation of the X-ray imaging apparatus, an X-ray generator 7, an exposure button 8 used by an operator for performing X-ray exposure, a display device 9 for producing an X-ray-image display and performing user interface relating to the operation, a storage 10 for storing various types of settings, X-ray images, and so forth, and a bus line 11 for connecting the above-described units with one another, the units forming the X-ray imaging apparatus.

The grid 4 is a plate formed by cutting a laminate formed by laminating lead plates and aluminum plates onto one another along a direction perpendicular to the laminated layers. The grid 4 is provided so that the lead plates that are provided in parallel with one another extend in a direction along which primary radiation travels. Therefore, the grid 4 can remove unnecessary scattered radiation emitted from the patient 2. An X-ray image of the grid 4 overlaps an X-ray image of the patient 2. However, the grid image does not interfere with making a diagnosis because a suitable frequency is selected from among spatial frequencies of the grid 4.

According to a first embodiment, there are three to eight parts of alternating laminates in the grid 4 per millimeter for a resonant spatial frequency of three to eight. In general, a smaller spatial frequency (or grid pitch) yields a clearer grid image. However, in this embodiment, the spatial frequency number (or grid pitch) is selected according to the pixel pitch of pixels for X-ray detection in the X-ray detector 5. The thickness of each lead plate of the grid 4 needs to be about 50 $\mu$m for blocking the scattered radiation with efficiency. For example, in the case where the pitch of the detector 5 is about 4 pixels/mm, the thickness of each lead plate should preferably be about 50 $\mu$m and the thickness of each aluminum plate should preferably be about 200 $\mu$m with reference to the grid pitch of 250 $\mu$m.

The AEC detector 12 according to this embodiment is arranged that it can make its exposure detection without affecting the image quality and the exposure dose, as explained below. The AEC detector 12 covers a small portion of the area of the X-ray detector 5, the small portion corresponding to a featureless area of the X-ray image such as the center part of the lungs of the patient 2, for example, so as not to increase the exposure dose. Further, the density of part of an obtained X-ray image, corresponding to the lungs, is appropriately adjusted by detecting the X-ray amount on the center part of the lungs. The AEC detector 12 becomes an artifact when it overlaps the X-ray image of the patient 2. Therefore, the AEC detector 12 is formed so that it only marginally blocks the X-rays. For example, the AEC detector 12 is formed as a flat-shaped chamber whose periphery is formed of a material that only marginally blocks the X-rays. The X-ray amount is detected by collecting a small number of electrical charges that are ionized in the chamber by the X-ray. In another case, the AEC detector 12 may be formed of a thin fluorescent plate, and fluorescence generated by the X-ray may be detected by using a multiplier phototube.

The operation of the X-ray imaging apparatus according to this embodiment will now be described.

First, preparations for performing AEC-pixel calibration are made. After removing the grid 4, the imaging unit 3 is uniformly irradiated with an X-ray, and an output from the AEC pixel is stored in the storage 10. This output is referred to as a grid-OFF-AEC-gain image. Then, the grid 4 is mounted, the imaging unit 3 is uniformly irradiated with another X-ray, and an output from the AEC pixel is stored in the storage 10. This output is referred to as a grid-ON-AEC-gain image. If required, various types of AEC-gain images are obtained and stored by changing the X-ray beam quality or the geometrical arrangement. In the case where the X-ray beam quality is changed, the grid contrast changes. Further, in the case where the geometrical arrangement is stored, the AEC image may change. These preparations may preferably be made at the same instant when the sensitivity characteristic of the X-ray detector 5 is corrected.

Figure 2:
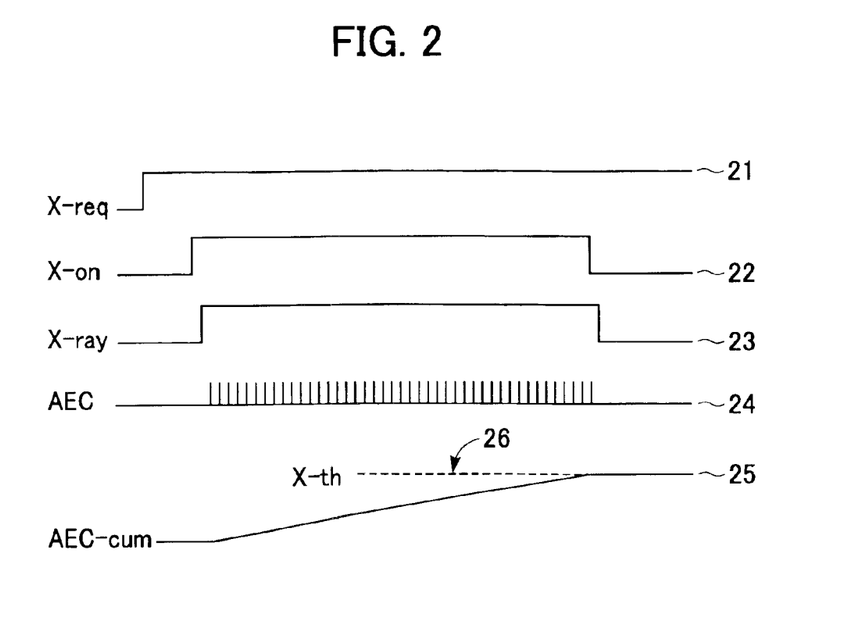
FIG. 2 is a flowchart illustrating the operation of the X-ray imaging apparatus.

Next, exposure sequences in the case where the grid 4 is mounted will be described with reference to FIGS. 1 and 2. As shown in FIG. 2, reference numeral 21 indicates an X-ray-exposure-request signal, reference numeral 22 indicates an X-ray-exposure-instruction signal, reference numeral 23 indicates an X-ray, reference numeral 24 indicates an AEC signal output from the AEC pixel, reference numeral 25 indicates an AEC-signal-integral value, and reference numeral 26 indicates the threshold value of the AEC-signal-integral value 25.

When the operator presses the exposure button 8 down, the X-ray-exposure request signal 21 is transmitted to the CPU 6 via the X-ray generator 7. Upon receiving the X-ray exposure request signal 21, the CPU 6 starts making preparations of the X-ray detector 5. When the preparations are made, the CPU 6 turns the X-ray exposure instruction signal 22 on and transmits it to the X-ray generator 7. Upon receiving the X-ray exposure instruction signal 22, the X-ray generator 7 makes the X-ray tube 1 operate so as to generate the X-rays 23. The X-rays 23 pass through the patient 2 and reaches the imaging unit 3. Further, the X-rays 23 pass through the grid 4 and reach the X-ray detector 5.

The CPU 6 samples an AEC image output from the AEC pixel included in the X-ray detector 5 every 0.5 msec. Then, the AEC image is calibrated by the grid-ON-AEC-gain image stored in the storage 10 and changed into the AEC signal 24 that is obtained in the case where the grid 4 is not used and the sensitivities of the AEC pixels are equal to one another.

The X-ray imaging apparatus of this embodiment uses the X-ray detector 5 including a phosphor that is in contact with a large area amorphous silicon sensor. This type of detector is a flat-panel detector (FPD). This X-ray imaging apparatus is a digital radiographic device that can directly digitize an X-ray image without using an optical system or the like. Another type of FPD that changes an X-ray into electrons by using amorphous selenium, lead iodide (PbI2), mercury iodide (HgI2), and so forth and that detects the electrons by using the large area amorphous silicon sensor can be used as another embodiment. Since these types of FPDs can radiograph not only a still image but also moving images, it is expected that these FPDs will be next generation digital radiographic devices.

In the case where one of the above-described FPDs are used as in this embodiment, detector elements for real-time reading are provided as the AEC detector 12, other than the pixels provided for detecting an image. These real-time reading detector elements are diverted from normal pixels on a solid-state-image pickup element and will be hereinafter referred to as AEC pixels. Signals output from the AEC pixels, the signals being integrated according to the geometrical arrangement of the AEC signals, will be hereinafter referred to as an AEC image.

A sensor used by the FPD includes several million pixels. The characteristic of each of the pixels is slightly different from one another. One of the important characteristics of the sensor functioning as an image sensor is a sensitivity characteristic. There is variation in the sensitivity characteristics of the AEC pixels as in the case of the variation in the sensitivity characteristics of the image sensor. This variation in the sensitivity characteristics may interfere with correct estimation of the X-ray amount. Therefore, the sensor of the FPD of this embodiment corrects the above-described characteristics as described below. Further, the characteristics of the pixels are substantially the same as one another.

The method for correcting the sensitivity characteristics of the AEC pixels is the same as a method for correcting the sensitivity characteristics of the normal pixels. The latter method will be described first. This method can be used for the FPD using amorphous selenium or the like.

First, a method for correcting a dark-current characteristic will be described before describing the method for correcting the sensitivity characteristics. Here, a dark current is a current that is measured when no signal is input to the sensor (the normal pixels) and that includes a random component and an offset component. If the dark current has no dependence on an input to the sensor, it becomes possible to correct the offset components of the pixels, the offset components being different from one another, by subtracting an image obtained in the case where a signal is input to the sensor from an image obtained in the case where no signal is input to the sensor. When an X-ray image obtained in the case where a signal is input to the sensor is determined to be $X_1(x,y)$ and a dark-current image obtained right after the X-ray image is determined to be $D_1(x,y)$, a first dark-current-correction image $C_{1X}(x,y)$ obtained after the dark-current correction can be described in Equation (1), where the signs x and y indicate the address of each of the pixels provided in two-dimensional arrangement.

$$C_{1X}(x,y)=X_1(x,y)-D_1(x,y) \qquad \text{Equation (1)}$$

Next, the method for correcting the sensitivity characteristics will be described. The sensitivity-characteristic correction is sometimes referred to as calibration. The sensitivity characteristic correction is performed for correcting variation in the sensitivity characteristics of the pixels forming the sensor. If the sensitivity characteristics are stationary, the sensitivity characteristics of the pixels, the sensitivity characteristics being different from one another, would be corrected by dividing the image obtained in the case where the signal is input to the sensor by an image obtained in the case where identical signals are input to the sensor. In the case where the image obtained in the case where the identical signals are input to the sensor is determined to be $C_W(x,y)$ and an X-ray-image component and a dark-current-image component included in the $C_W(x,y)$ are determined to be $W(x,y)$ and $D_W(x,y)$, respectively, a corrected image $C_1(x,y)$ subjected to the sensitivity-characteristic correction can be described by the Equations (2) and (3).

$$C_1(x,y) = \frac{\overline{C_W(x,y)}}{C_W(x,y)} \cdot C_{1X}(x,y) \qquad \text{Equation (2)}$$

$$= \frac{\overline{W(x,y)-D_W(x,y)}}{W(x,y)-D_W(x,y)} \cdot \{X_1(x,y)-D_1(x,y)\} \qquad \text{Equation (3)}$$

The method for correcting the sensitivity characteristics of the AEC pixels is the same as the above-described method for correcting the sensitivity characteristics of the normal pixels. Therefore, the sensitivity characteristics of the AEC pixels can be calibrated according to Equation (2). The grid-ON-AEC-gain image is determined to be $C_W(x,y)$, the AEC image is determined to be $C_{1X}(x,y)$, and the AEC signal 24 that is a corrected-image signal subjected to the sensitivity correction is determined to be $C_1(x,y)$. In general, the X-ray imaging apparatus emits identical X-rays for the sensitivity-characteristic correction. However, according to the dose level for X-ray image diagnosis, quantum noise proportionate to the square root of the number of X-ray quanta overlaps the X-ray image. Since this noise is inevitable, the quantum noise also overlaps $C_W(x,y)$. In this case, the precision of the sensitivity-characteristic correction may decrease due to the quantum noise overlapping $C_W(x,y)$. In this embodiment, therefore, X-ray exposure is performed a plurality of times and the average of the obtained X-ray images is calculated for the sensitivity-characteristic correction. Further, the number of effective X-ray quanta included in $C_W(x,y)$ is increased, whereby the precision of the sensitivity-characteristic correction increases.

After that, the CPU 6 compares the AEC-signal integral value obtained by integrating the AEC signal to the threshold value 26 that is predetermined by the operator. When the AEC-signal integral value reaches the threshold value 26, the CPU 6 turns the X-ray exposure instruction signal 22 off and transmits the signal 22 to the X-ray generator 7 via the bus line 11. The X-ray generator 7 makes the X-ray tube 1 stop generating X-rays, whereby the exposure sequence is terminated.

When X-ray exposure is performed in the case where the grid 4 is removed, an obtained AEC image is calibrated by the grid-OFF-AEC-gain image stored in the storage 10 and changed into the AEC signal 24 that is obtained when the grid 4 is not used and the sensitivities of the AEC pixels are the same as one another. The method of calibration is the same as that of the sensitivity-characteristic correction performed for the FPD. The calibration is performed according to Equation (2). Similarly, in the case where the X-ray beam quality or the geometrical arrangement is changed, the calibration is performed by using a corresponding AEC image.

In this embodiment, the AEC pixels are included in the X-ray detector 5. However, this embodiment does not limit the scope of the present invention. For example, the AEC pixels can be provided between the grid 4 and the X-ray detector 5 as in the case of the known AEC detector as long as the characteristics of the AEC pixels change according to the condition of the grid 4.

Further, according to this embodiment, the plurality of AEC-gain images are stored beforehand, and the image complying with the AEC-image obtainment criteria is selected. However, the image does not necessarily fully comply with the criteria. That is to say, the AEC-gain images being closest to the AEC-image obtainment criteria can be selected. In the case where correct calibration is required, AEC-gain images complying with various types of the AEC-image obtainment criteria, respectively, may be stored beforehand for estimating a predetermined AEC-gain image by calculation. For instance, if an AEC-gain image obtained in the case where the tube voltage is 80 kVp and an AEC-gain image obtained in the case where the tube voltage is 120 kVp are provided, it would be easy to estimate an AEC-gain image obtained in the case where the tube voltage is 100 kVp by calculation. In another case, AEC-gain images complying with various types of grids that can be mounted may be stored.

Since the AEC detector 12 requires some space, the AEC detector 12 may interfere with miniaturization of the imaging unit 3. Further, since the AEC detector 12 has to detect extremely low-level noise either in the case where the AEC detector 12 has the air tank or the case where the AEC detector 12 has the fluorescent plate, the AEC detector 12 can be expensive. Although the AEC detector 12 only marginally blocks the X-rays, it does block some X-rays for measuring the X-ray amount, requiring the increase of the exposure dose and generating artifacts. The AEC detector 12 can be provided behind the X-ray detector 5 for solving the above-described problems. In this case, however, the quantum efficiency of the X-ray detector 5 improves, so that X-rays hardly pass through the X-ray detector 5. Subsequently, it becomes difficult to measure the X-ray amount with precision. Further, since the proportion of X-rays that pass through the X-ray detector 5 changes according to the energy of the X-rays, it also becomes difficult to measure the X-ray amount with precision.

For solving the above-described problems, detector elements for real-time reading are integrated into the solid-state image pickup element, near the pixels used for image detection. For example, TFT-detector elements can be formed in clearances among the pixels of the large-area amorphous-silicon sensor is used.

Figure 3:
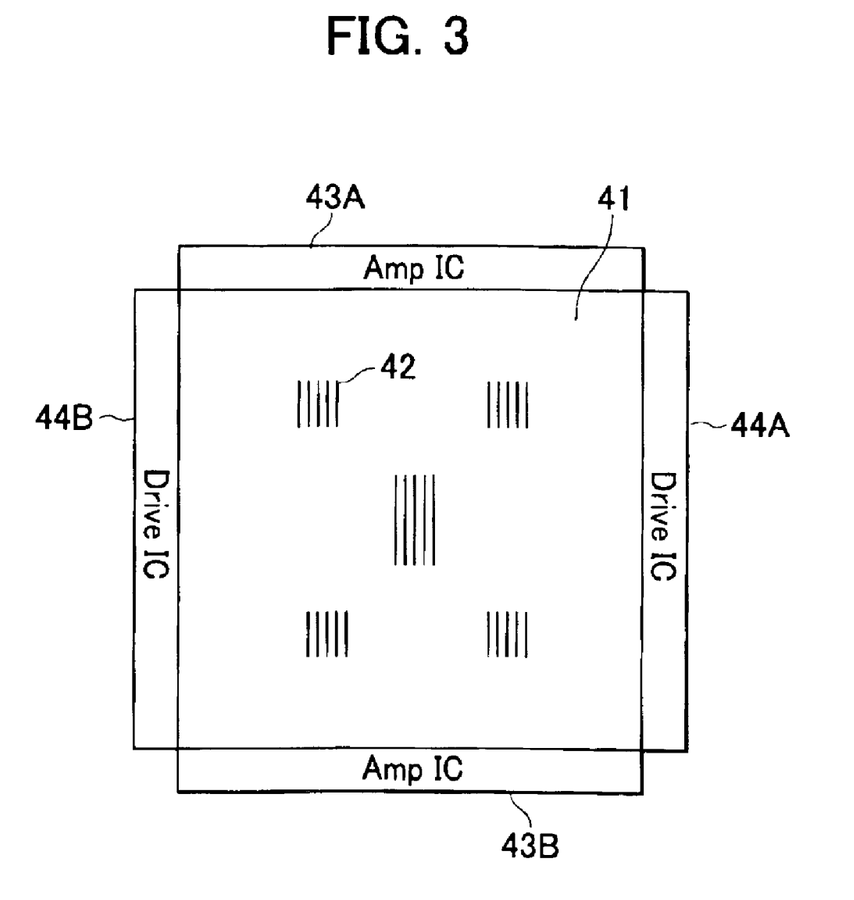
FIG. 3 illustrates an X-ray detector having stripes of thin film transistor (TFT) detector elements integrated therein.

FIG. 3 shows the configuration of the X-ray detector 5 for solving the above-described problems. As shown in this drawing, the TFT-detector elements are integrated into the FPD. In this drawing, an FPD 41 functions as an X-ray detector, the TFT-detector elements include stripes 42, an amplifier IC 43A reads at least one of the pixels provided on the FPD, a second amplifier IC 43B reads at least one of the pixels provided on the FPD, a drive IC 44A designates at least one of the pixels on the FPD, and a second drive IC 44B designates at least one of the pixels on the FPD.

In the case where the AEC pixels are integrated into the solid-state image pickup element, the AEC pixels have to be arranged relative to the normal pixels of the solid-state image pickup element, such that the size of each of the AEC pixels is substantially the same as that of the normal pixel. For example, in the case where the normal pixels are read in non-destructive manner, the size of the AEC pixel is the same as that of each normal pixel, so that the width of the AEC pixel, the AEC pixel being formed between the normal pixels, does not exceed the width of the normal pixel. For example, the width and length of each of the stripes of TFT-detector elements shown in FIG. 3 are 40 $\mu$m and 20 mm, respectively.

A predetermined area is required for obtaining a correct AEC signal. Therefore, a plurality of the AEC pixels is used so that an area that is the same as that of the known AEC detector can be detected. For example, as shown in FIG. 3, five TFT-detector elements are grouped as one lighting field. A plurality of the lighting fields is provided, and at least one of them is selected according to an objective. However, near real-time reading is necessary for performing the AEC. Since the length of time required for exposure is from several msec to about 1 second, it must be arranged that the reading of real time, the real time being 5 msec or less, if possible, about 0.5 msec, is performed. Considering the hardware cost in addition to the time limit, it is advantageous to minimize the number of AEC pixels.

However, as shown in the above-described embodiment, if the number of the AEC pixels is limited, signals detected by the AEC pixels and those detected by the normal pixels often do not match. That is to say, the AEC image and the image obtained by the normal pixels often do not agree with each other. This is a statistical problem caused by the fact that the average of too few samples cannot represent population mean. In particular, this problem becomes significant in the case where the grid 4 is used. The grid density is from about 3 to 8 pixels per millimeter and the pixel density of the solid-state image-pickup element is usually from 2 to 5 pixels per millimeter. That is to say, both the densities are close to each other. Subsequently, one of the AEC pixels may be blocked by the lead plate, so that an X-ray image does not reach the AEC pixel. On the other hand, the X-ray image may hardly be attenuated and reach another one of the AEC pixels. In this case, variation is generated in signals output from the AEC pixels, and it may become difficult for the operator to determine which signal is to be used. This is another statistical problem caused by the fact that estimating the population mean by using the samples is difficult in the case where the number of the samples is low and the value of population variance is high. This problem becomes significant in the case where the AEC pixels are provided in lines, and the direction along which the AEC pixels are provided becomes parallel to the orientation of the lead plates, as shown in FIG. 3.

According to a second embodiment, however, since gain correction is performed for each of the AEC pixels, the sensitivities of the AEC pixels substantially increase, even though part of the AEC pixels is blocked by the grid 4. Consequently, all the AEC pixels can be used without being hampered by the sensitivity variation thereof. Therefore, correct AEC can be performed even though the direction along which the AEC pixels are provided becomes substantially parallel to the orientation of the stripes of the grid 4.

According to the present invention, a signal detected by the AEC pixels is calibrated according to the grid state, for example, whether or not the grid is mounted or removed. Subsequently, it becomes possible to estimate the X-ray-incident amount with precision and perform appropriate AEC regardless of the grid state.

Additional Embodiments

It is to be understood that the object of the present invention can also be achieved by supplying a storage medium storing program code of software for implementing the functions of the apparatus or system according to the first or second embodiment to an apparatus or system so that a computer (CPU, MPU, etc.) of the apparatus or system reads and executes the program code stored in the storage medium.

In that case, the program code itself, read from the storage medium, achieves the functions of the first or second embodiment, and thus the storage medium storing the program code and the program code itself constitute the present invention.

The storage medium for providing the program code may be, for example, a Read Only Memory (ROM), a floppy disk, a hard disk, an optical disk, a magneto-optical disk, a CD-ROM, a CD-R, a magnetic tape, a non-volatile memory card, etc.

Furthermore, not only by the computer reading and executing the program code, but also by the computer executing part of or the entire process utilizing an operation system (OS), etc. running on the computer based on instructions of the program code, the functions of the first or second embodiment may be achieved. The latter is also one of the embodiments of the present invention.

Furthermore, the program code read from the storage medium may be written to a memory of a function extension board inserted in the computer or a function extension unit connected to the computer. The functions of the first or second embodiment may be realized by executing part of or the entire process by a CPU, etc. of the function extension board or the function extension unit based on instructions of the program code. This is also one of embodiments of the present invention.

When the present invention is applied to a program or a storage medium storing the program.

It is to be understood that the present invention may also be applied to a system including a plurality of apparatuses (e.g., X-ray generating apparatuses, X-ray imaging apparatuses, image processing apparatuses, and interface apparatuses, etc.) and to a single apparatus in which functions of these apparatuses are integrated. When the present invention is applied to a system including a plurality of apparatuses, the apparatuses communicate with one another via, for example, electrical, optical, and/or mechanical means, and/or the like.

Furthermore, the present invention may also be applied to an image diagnosis aiding system including a network (Local Area Network (LAN) and/or Wide Area Network (WAN), etc.).

The present invention thus achieves the above-described object as described above.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An X-ray imaging apparatus comprising:

X-ray generation means for emitting X rays;

an X-ray detector on which a grid selected from a plurality of different types of grids is removably mountable, wherein said X-ray detector receives the X-rays emitted from said X-ray generation means, and wherein said X-ray detector obtains X-ray image data;

said X-ray detector including an automatic exposure control (AEC) detector which includes plural exposure detection elements, said AEC detector for detecting the quantity of X-rays emitted from said X-ray generation means and for outputting a signal based on the detected quantity; and driving means for driving said X-ray generation means based on the signal output from said AEC detector, wherein a gain of the exposure detection elements is corrected by gain-correction data according to the selected grid in said AEC detector.

2. An X-ray imaging apparatus according to claim 1, wherein the gain of the exposure detection elements is corrected by gain-correction data according to an unmounted grid state in the case that the grid is not mounted.

3. An X-ray imaging apparatus according to claim 1, further comprising:

storing means to store a plurality of different types of gain-correction data;

wherein said AEC detector selects the gain-correction data according to whether one of said plurality of different types of grids is mounted.

4. An X-ray imaging apparatus according to claim 3, wherein said AEC detector further comprises gain-correction data calculation means and wherein said AEC detector calculates the gain-correction data based on the gain-correction data stored in the storing means, in the case where no gain-correction data corresponding to the selected grid.

5. An X-ray imaging apparatus according to claim 1, wherein said exposure detection elements are integrated into said X-ray detector.

6. An X-ray imaging apparatus according to claim 1, wherein said AEC detector further comprises a plurality of pixels and wherein each pixel is formed as a detector element that can be read in non-destructive manner.

7. An X-ray imaging apparatus according to claim 1, wherein said AEC detector further comprises a plurality of pixels and wherein each pixel is formed as a thin film transistor (TFT)-detector.

8. An X-ray imaging apparatus according to claim 1, wherein said control means reads said signal output from said AEC detector in a cycle of 5 msec or less.

9. An X-ray imaging apparatus according to claim 1, wherein the AEC detector further comprises a plurality of pixels formed as stripes of detector elements provided so as to be substantially parallel to the orientation of stripes of said grid.

10. A method for controlling an X-ray imaging apparatus comprising the steps of:

emitting X-rays;

changing the X-rays received through a selected grid into X-ray image data;

detecting a quantity of emitted X-rays using an AEC detector and outputting a signal based on the detected quantity; and stopping said X-ray emission based on the signal, wherein a gain of exposure detection elements forming a part of said AEC detector is corrected by gain-correction data according to the selected grid in said AEC detector.

11. Computer-executable process steps stored on a computer-readable medium, said computer-executable process steps for making a computer perform a method for controlling an X-ray imaging apparatus, said computer-executable process steps comprising process steps executable to perform a method according to claim 10.

12. A computer-readable medium which stores computer-executable process steps, the computer-executable process steps for making a computer perform a method for controlling an X-ray imaging apparatus, said computer-executable process steps comprising process steps executable to perform a method according to claim 10.

* * * * *